United States Patent [19]

Burress

[11] E Re. 30,157

[45] Reissued Nov. 20, 1979

[54] XYLENE ISOMERIZATION

[75] Inventor: George T. Burress, Somerville, N.J.

[73] Assignee: Mobil Oil Corporation, New York, N.Y.

[21] Appl. No.: 861,814

[22] Filed: Dec. 19, 1977

Related U.S. Patent Documents

Reissue of:

[64] Patent No.: 3,856,873
Issued: Dec. 24, 1974
Appl. No.: 397,194
Filed: Oct. 13, 1973

[51] Int. Cl.[2] ..... C07C 5/24

[52] U.S. Cl. ..... 585/411; 585/322; 585/481; 585/486

[58] Field of Search ..... 260/668 A

[56] References Cited

U.S. PATENT DOCUMENTS

| | | | |
|---|---|---|---|
| 2,795,630 | 6/1957 | Lien et al. | 260/668 R |
| 3,646,236 | 2/1972 | Keith et al. | 260/672 T |
| 3,691,247 | 9/1972 | Billings | 260/668 A |
| 3,751,504 | 8/1973 | Keown et al. | 260/672 T |
| 3,756,942 | 9/1973 | Cattanach | 208/132 |
| 3,761,389 | 9/1973 | Rollman | 208/64 |
| 3,790,471 | 2/1974 | Arqzuer et al. | 260/672 T |

*Primary Examiner*—C. Davis
*Attorney, Agent, or Firm*—Charles A. Huggett; Raymond W. Barclay; Thomas S. Szatkowski

[57] ABSTRACT

Mixtures of $C_8$ aromatic hydrocarbons are contacted in vapor phase with acid zeolite ZSM-5. The xylene content is thereby isomerized and the ethyl benzene content of the charge is converted in a manner which results in net increase of aromatic rings.

5 Claims, 1 Drawing Figure

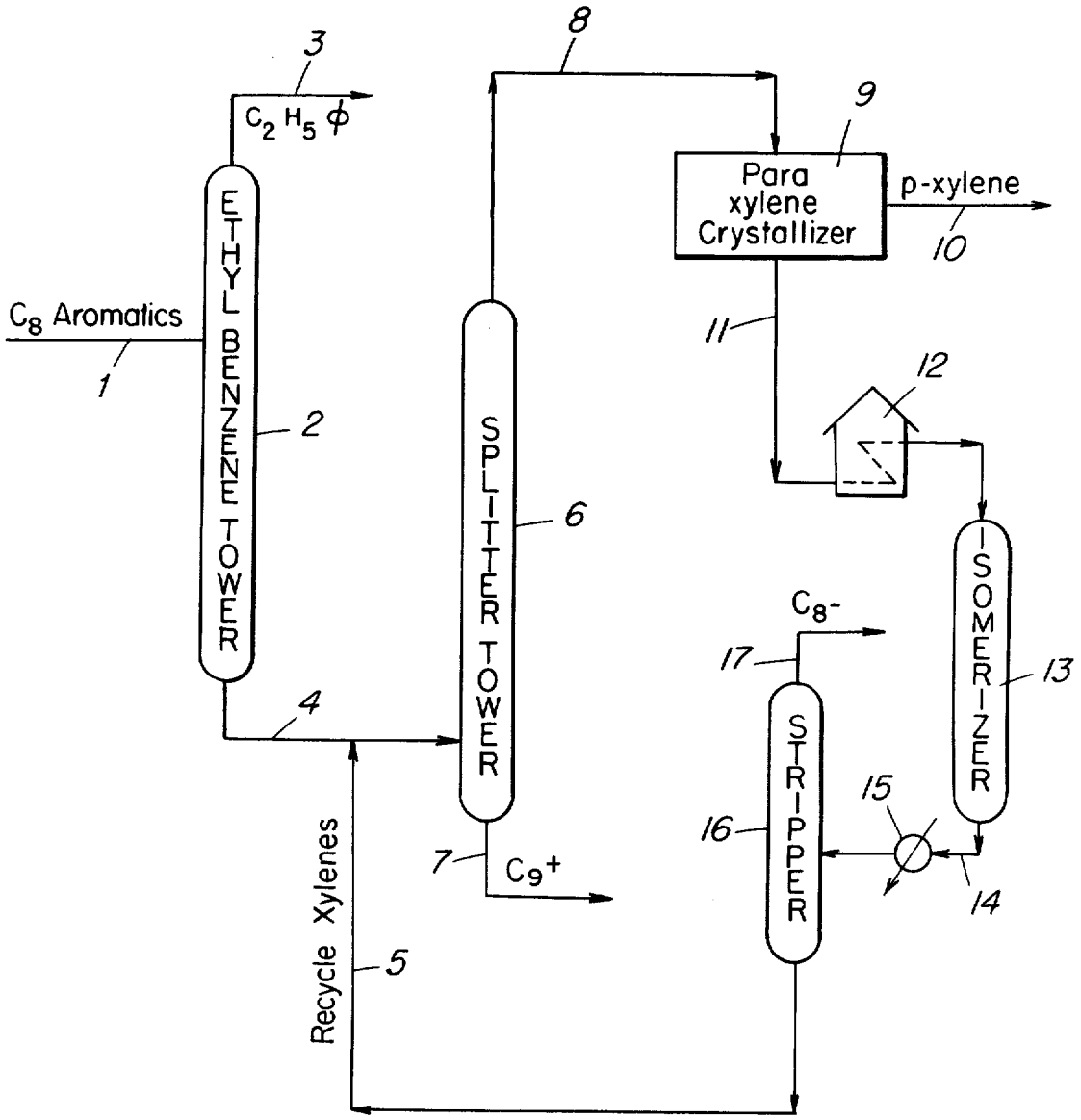
3
$C_2H_5\phi$
8
9
Para xylene Crystallizer
p-xylene
10
$C_8$ Aromatics
1
ETHYL BENZENE TOWER
2
SPLITTER TOWER
6
11
12
ISOMERIZER
13
$C_8$-
17
STRIPPER
16
15
14
4
7
$C_9$+
Recycle Xylenes
5

XYLENE ISOMERIZATION

Matter enclosed in heavy brackets [ ] appears in the original patent but forms no part of this reissue specification; matter printed in italics indicates the additions made by reissue.

BACKGROUND OF THE INVENTION

Xylenes are found in fractions from coal tar distillate, petroleum reformates and pyrolysis liquids in admixture with other compounds of like boiling point. The aromatic components are readily separated from non-aromatics by solvent extraction. Distillation provides a fraction consisting essentially of $C_8$ aromatics. As will appear below, o-xylene is separable from other $C_8$ aromatics by fractional distillation, and p-xylene is separable by fractional crystallization. Present demand is largely for p-xylene and it has become desirable to convert m-xylene, the principal xylene present in the feed stream, to the more desired p-xylene.

Since the announcement of the first commercial installation of Octafining in Japan in June, 1958, this process has been widely installed for the supply of p-xylene. See "Advances in Petroleum Chemistry and Refining" volume 4, page 433 (Interscience Publishers, New York 1961). That demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

| | Freezing Point °F. | Boiling Point °F. | Density Lbs./U.S. Gal. |
|---|---|---|---|
| Ethyl benzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources at present are catalytically reformed naphthas and pyrolysis distillates. The $C_8$ aromatic fractions from these sources vary quite widely in composition but will usually be in the range 10 to 32 wt. percent ethyl benzene with the balance, xylenes, being divided approximately 50 wt. percent meta, and 25 wt. percent each of para and ortho.

In turn, calculated thermodynamic equilibra for the $C_8$ aromatic isomers at Octafining conditions are:

| Temperature | | 850° F. |
|---|---|---|
| Wt. % Ethyl benzene | | 8.5 |
| Wt. % para xylene | | 22.0 |
| Wt. % meta xylene | | 48.0 |
| Wt. % ortho xylene | | 21.5 |
| | TOTAL | 100.0 |

An increase in temperature of 50° F. will increase the equilibrium concentration of ethyl benzene by about 1 wt. percent, ortho-xylene is not changed and para and meta xylenes are both decreased by about 0.5 wt. percent.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yield of the desired xylenes.

Octafining process operates in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

The isomerizer unit itself is most simply described as a single reactor catalytic reformer. As in reforming, the catalyst contains a small amount of platinum and the reaction is carried out in a hydrogen atmosphere.

Octfiner unit designs recommended by licensors of Octafining usually lie within these specification ranges:

| Process Conditions | |
|---|---|
| Reactor Pressure | 175 to 225 PSIG |
| Reactor Inlet Temperature Range | 830-900° F. |
| Heat of Reaction | Nil |
| Liquid Hourly Space Velocity | 0.6 to 1.6 Vol/Vol/Hr. |
| Number of Reactors, Downflow | 1 |
| Catalyst Bed Depth, Feet | 11 to 15 |
| Catalyst Density, Lb/Cu. Ft. | 38 |
| Recycle Circulation, Mols Hydrogen/Mol Hydrocarbon Feed | 7.0 to 14.0 |
| Maximum Catalyst Pressure Drop, PSI | 20 |

It will be apparent that under recommended design conditions, a considerable volume of hydrogen is introduced with the $C_8$ aromatics. In order to increase throughput, there is great incentive to reduce hydrogen circulation with consequent increase in aging rate of the catalyst. Aging of the catalyst occurs through deposition of carbonaceous materials on the catalyst with need to regenerate by burning off the coke when the activity of the catalyst has decreased to an undesirable level. Typically the recommended design operation will be started up at about 850° F. with reaction temperature being increased as needed to maintain desired level of isomerization until reaction temperature reaches about 900° F. At that point the isomerizer is taken off stream and regenerated by burning of the coke deposit.

Because of its capability to convert ethyl benzene, Octafining can accept a charge stream which contains that component. Normally, a portion of the ethyl benzene is removed by fractional distillation before the charge is processed. If no attempt is made to reduce ethyl benzene below a few percent by weight, this can be accomplished inexpensively and the ethyl benzene recovered is in usable form as a relatively pure chemical, e.g., for dehydrogenation to styrene.

The Octafiner is in a "loop" which includes means for separation of desired xylenes; p-xylene by crystallization and, possible, o-xylene by distillation. The $C_8$ stream stripped of desired xylenes returns to the Octafiner where more of the desired xylenes are generated, for example by isomerization of m-xylene. It will be apparent that ethyl benzene will tend to build up in the loop as other components are removed. The Octafining catalyst has capability for converting ethyl benzene, thus counteracting that tendency. It, the Octafining catalyst, has the disadvantage that it is a hydrocracking catalyst due to the acid function of its silica/alumina base and its content of hydrogenation/dehydrogenation metal of the platinum group. In addition to converting ethyl benzene, this catalyst also causes net loss of xylenes.

Other catalysts have recently been identified as behaving in the same fashion as Octafining catalyst for isomerization of xylenes in $C_8$ aromatic fractions accompanied by conversion of ethyl benzene. These new catalysts include zeolites of the ZSM-5 type, zeolite ZSM-12 [and zeolite ZSM-21], *zeolite ZSM-35 and zeolite ZSM-38. ZSM-5* type includes zeolite ZSM-5 as described in Argauer and Landolt Pat. No. 3,702,886, dated Nov. 14, 1972 and zeolite ZSM-11 as described in Chu Pat. No. 3,709,979, dated Jan. 7, 1973 and variants thereon. Zeolite ZSM-12 is described in German Offenlegungsschrift No. 2,213,109. The activity of these catalysts for the stated purpose and of [ZSM-21 is] *zeolites ZSM-35 and ZSM-38 (there identified as ZSM-21) are* described and claimed in copending application of R. A. Morrison, Ser. No. 397,039, filed Sept. 13, 1973, the disclosure of which is hereby incorporated by reference.

In general, Octafining catalyst and the zeolite catalysts referred to above behave in about the same manner, except for their aging characteristics; decline of activity with time on stream.

A typical charge to the isomerizing reactor (effluent of crystallizer for separation of p-xylene) may contain 17 wt. percent ethyl benzene, 65 wt. percent m-xylene, 11 wt.% p-xylene and 7 wt. percent o-xylene. The thermodynamic equilibrium varies slightly with temperature in a system in which o-xylene is separated in the loop by fractional distillation prior to the crystallizer. The objective in the isomerization reactor is to bring the charge as near to theoretical equilibrium concentrations as may be feasible consistent with reaction times which do not give extensive cracking and disproportionation.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethylene and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.), has but a very small effect on ethyl benzene approach to equilibrium.

Concurrent loss of ethyl benzene to other molecular weight products relates to percent approach to equilibrium. Products formed from ethyl benzene include $C_6$+naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecules weight products varies with contact time. By-products include naphthenes, toluene, $C_9$ aromatics and $C_5$ and lighter hydrocracking products.

Ethyl benzene has been found responsible for a relatively rapid decline in catalyst activity of Octafining catalyst and this effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

A more recent development than Octafining is Low Temperature Isomerization (LTI) as described in Wise Pat. No. 3,377,400, dated Apr. 9, 1968. That process is particularly effective when the zeolite catalyst employed is ZSM-4 as described in Bowes, et al. U.S. Pat. No. 3,578,723, dated May 11, 1971.

The advantages of LTI rest in its capbility to isomerize xylenes in liquid phase at relatively low temperatures and the lack of necessity for hydrogen pressure in the reactor. The zeolite catalyst, particularly ZSM-4, ages very slowly even with hydrogen or a hydrogenation/dehydrogenation metal component of the catalyst. However, LTI has one disadvantage. It leaves ethyl benzene unchanged.

Because the ethyl benzene content of $C_8$ aromatic fractions is unchanged in LTI operations as practiced heretofore, such operations incur severe costs in capital investment and in operating expense to dispose of the ethyl benzene in order that it shall not build up in the system. Because of the minor difference in boiling point between ethyl benzene and certain of the xylenes, complete removal of ethyl benzene from the charge is prohibitive in cost. The practical way to handle this component is to provide an additional distillation column in the loop to remove ethyl benzene at substantial cost.

THE INVENTION

It has now been found that catalysts which are the acid forms of zeolite ZSM-5 type, zeolite ZSM-12 [or zeolite ZSM-21], *zeolite ZSM-35 or zeolite ZSM-38* provide $C_8$ aromatic isomerization catalysts which not only are very active and selective for shifting methyl groups on xylenes, but also convert ethyl benzene in a manner not previously observed for feeds of this type, if the process is conducted in the absence of substantial added hydrogen.

It is, accordingly, a primary object of this invention to isomerize the xylene content of $C_8$ aromatic fractions, but also to convert the ethyl benzene content thereof in a novel and unexpected fashion.

As will be readily understood, the type of ethyl benzene conversion typical of Octafining (and also observed with metal ZSM-5 in the presence of hydrogen) cannot occur when hydrogen is not supplied to the reactor. It will be recalled that the conversion of ethyl benzene in Octafining proceeds by hydrogenation to ethyl cyclohexane which undergoes rearrangement to dimethyl cyclohexane. Dehydrogenation of that compound yields xylenes.

Despite the fact that the classical (Octafining) type of ethyl benzene conversion is impossible under the conditions characteristic of this invention, the conversion of that compound in the process of the invention does result in enhanced yeild of desired aromatic compounds. While not wishing to be limited by theoretical considerations, it is postulated that the alkyl side chain of ethyl benzene is cracked off the ring by the present catalysts at the conditions employed. This yeilds benzene, a valuable by-product, and ethylene. The increase in number of aromatic rings is believed to occur by way of the reaction described in U.S. Pat. application Ser. No. 153,855, filed June 16, 1971, the disclosure of which is hereby incorporated by this reference. By whatever mechanism the reaction proceeds, the ethylene will react over HZSM-5 and other zeolites recited above to form benzene and alkyl benzenes, thus generating additional aromatic molecules from the conversion of the ethyl benzene in addition to the benzene resultant from stripping off the alkyl group. It is perhaps surprising that this reaction will proceed in a system so heavily predominating in aromatic ring compounds which could be thought inhibitory of the reaction.

The above objects are attained in a process illustrated in the single FIGURE of drawings which is a diagrammatic representation of apparatus suited to practice of the invention.

A mixture of $C_8$ aromatics is supplied to the system by line 1, as from solvent extraction of a narrow cut taken by distillation of product of reforming a petroleum naphtha over platinum on alumina catalyst in the presence of hydrogen. The feed passes to distillation in ethyl benzene tower 2, from which a portion of the ethyl benzene content is taken overhead by line 3. It is impracticably expensive to attempt removal of substantially all of the ethyl benzene by tower 2. The amount removed as essentially pure ethyl benzene, suitable for charge to such operations as dehydrogenation to styrene, will depend on exact nature of the charge and demand for different products.

Bottoms from tower 2 are constituted by the xylenes present in the charge and a reduced content of ethyl benzene. This mixture passes by line 4 and is blended with recycle xylenes, derived in a manner presently to be described, from line 5. The blended stream is admitted to splitter tower 6 from which a heavy end is withdrawn by line 7. In the embodiment shown, that heavy end is constituted by $C_9$+aromatics derived from the minor side reaction of transalkylation in the isomerizer. Alternatively, when it is desired to recover o-xylene as a separate product, splitter tower 6 may be operated to include o-xylene in the bottoms which are then passed to distillation for separation of o-xylene from $C_9$+aromatics (not shown).

The overhead of splitter tower 6 passes by line 8 to means for separation of p-xylene. In the embodiment illustrated, p-xylene is separated by fractional crystallization in crystallizer 9, involving chilling and filtration of p-xylene crystals from the liquid phase, for example, in the manner described by Machell et al. U.S. Pat. No. 3,662,013, dated May 9, 1972. It will be understood that other systems for p-xylene separation may be used in a plant for practice of this invention, e.g., selective sorption as described in Cattanach patent No. 3,699,182, dated Oct. 17, 1972. By whatever means separated, high purity p-xylene is withdrawn as product by line 10.

The stream of $C_8$ aromatics of reduced p-xylene content is withdrawn from crystallizer 9 by line 11, passed through heater 12 and admitted to catalytic isomerizer 13 where it is contacted at reaction conditions with the acid form of ZSM-5 type zeolite or zeolite ZSM-12 [or zeolite ZSM-21], *zeolite ZSM-35 or zeolite ZSM-38.*

The principal reaction in isomerizer 13 is shifting of methyl groups in xylene molecules toward the equilibrium concentrations of the three xylenes. In addition to xylene isomerization, secondary reactions of transalkylation occur to produce benzene, toluene, polyethyl benzenes and polymethyl benzenes. Important for the purposes of this invention is cracking of the side chain of ethyl benzene to yield benzene and ethylene. At the elevated temperatures contemplated by this invention, ethylene will react in the manner above described to produce aromatic compounds, primarily benzene.

The isomerizate produced in isomerizer 13 is transferred by line 14 through heat exchanger 15 to stripper 16. The light ends of the isomerizate (benzene, toluene and normally gaseous hydrocarbons) are taken overhead by line 17 from stripper 16 and the balance passes by line 5 to be blended with fresh feed and recycled in the process.

The catalyst is prepared by converting the zeolite to "acid form" by calcination which converts tetraalkylammonium cations characteristic of these zeolites to protons by decomposition of the substituted ammonium cations. Additional protons and various metal cations may be substituted for the sodium cations present in the zeolites as formed by base exchange in conventional manner. It is essential to success in the present process that the zeolite catalyst be at least partially in the acid form, that is, that at least a portion of the cation positions be occupied by protons. Metal cations of various types may occupy the other sites if desired.

Since the process is conducted in the absence of added hydrogen, there is no need for metals of the transition groups such as nickel, platinum, palladium, etc. These metals may be present, but as now understood, the process appears to be unaffected by such cations.

The zeolite crystals are preferably embedded in a bonding material to provide pellets of desired size and resistance to attrition. A suitable binder is alumina. In order to provide a preponderance of the active zeolite, the binder is a minor constituent of the composite. A particularly preferred catalyst is constituted by pellets of 35 wt. percent alumina and 65 wt. percent of the acid form of type ZSM-5 zeolite, zeolite ZSM-12 [or zeolite ZSM-21], *zeolite ZSM-35 or zeolite ZSM-38.*

The isomerization process of this invention is operated in the vapor phase at temperatures of 500° F. to 1,000° F. under pressure below that which will liquefy the charge. Aside from the need to maintain vapor phase conditions, pressure does not seem to be a critical parameter and will be dictated in the usual case by economic and engineering considerations. Pressures may range upwards from atmospheric pressure (0 pounds per square inch, gauge) but will normally be sent somewhat higher to accommodate the process to relatively small reaction vessels. Excessively high pressures, above about 1,000 p.s.i.g. will be generally undesirable, though fully operative, because of the great strength of reaction vessel walls required at high pressures, making the equipment unnecessarily expensive and requiring expensive compression stages.

Space velocities will vary in the range of 0.5 to 250 unit weights of charge per unit weight of zeolite per hour (weight hourly space velocity, WHSV). In general, temperature and WHSV will be coordinated to provide a desired severity which will provide an adequate degree of xylene isomerization and ethyl benzene conversion without excessive losses to by-products. Thus, temperatures in the lower part of the temperature range will normally call for low space velocities.

EXAMPLE 1

The catalyst employed was 65 wt. percent HZSM-5 (the acid form of ZSM-5 prepared by ammonium exchange and calcining) in 35 wt. percent alumina. The run was conducted at 950° F., atmospheric pressure and 21 WHSV based on zeolite content only of the catalyst. The nature of the conversion will be apparent from a tabulation of feed and product compositions:

TABLE I

| | Feed, wt. % | Product, wt. % |
|---|---|---|
| Light Ends | — | 0.1 |
| Ethyl benzene | 25.8 | 6.2 |
| Benzene | 0.0 | 11.8 |
| Toluene | 1.0 | 4.9 |
| p-xylene | 10.2 | 17.6 |
| m-xylene | 53.1 | 39.3 |
| o-xylene | 9.9 | 18.9 |
| $C_9$+ | 0.0 | 1.2 |
| TOTAL XYLENES | 73.2 | 75.8 |

It will be seen that under the relatively high severity of this run, major conversion of ethyl benzene is accomplished. The very extensive reaction of ethyl benzene on this acid catalyst, accompanied by isomerization of the xylenes is highly advantageous for commercial operations,

EXAMPLE 2

Using the same catalyst as that described in Example 1, a run was made at 540° F., pressure of 150 p.s.i.g. and WHSV of 4. The results shown in Table II report conversion after more than 10 hours on stream.

TABLE II

| | Feed wt. % | Product, wt. % | Wt. % of xylene portion of product |
|---|---|---|---|
| Ethyl benzene | 16.2 | 15.0 | — |
| Benzene | — | 0.4 | — |
| Toluene | — | 0.2 | — |
| p-xylene | — | 20.2 | 24.1 |
| m-xylene | 61.2 | 45.1 | 53.9 |
| o-xylene | 22.6 | 18.4 | 22.0 |
| $C_9$+ | — | 0.7 | — |

EXAMPLE 3

This example illustrates effectiveness of zeolites according to the invention which have been treated to incorporate both protons and metal cations. Zeolite ZSM-5 was base exchanged with ammonium and nickel salts, incorporated in alumina to form a composite catalyst containing 65 wt. percent NiHZSM-5 and 35 wt. percent alumina. The composite catalyst analyzed 0.68 wt. percent nickel and 0.05 wt. percent sodium. The composite was formed into one-sixteenth inch extrudate and admixed with tabular alumina (inert) to facilitate operation at high space velocity. The admixture contained 12.5 vol. percent of NiHZSM-5/alumina composite and 87.5 vol. percent of tabular alumina.

The conditions and product yield are set out in Table III.

TABLE III $C_8$ Aromatics Isomerization NiHZSM-5 Catalyst
Charge, wt. %: 17.2 EB, 10.7 p-xyl, 65.6 m-xyl, 6.5 o-xyl

| | | |
|---|---|---|
| Temperature, °F. | 600 | |
| Pressure, PSIG | 200 | |
| WHSV (on zeolite) | 2 | |
| $H_2$/HC | 0 | |
| Time on Stream, Hrs. | 21.4 | |
| Material Balance | 95.7 | |
| Product Distribution wt. % | | |
| $C_1$ | | — |
| $C_2$ | | 0.03 |
| $C_3$ | | 0.1 |
| i-$C_4$ | | — |
| n-$C_4$ | | — |
| i-$C_3$ | | — |
| $C_6H_6$ | | 2.1 |
| $C_7$ (alkyl) | | — |
| Toluene | | 1.6 |
| $C_8$ (alkyl) | | — |

| $C_8$ aromatics on total and on $C_9$ aromatics | Total | | $C_8$ Ar |
|---|---|---|---|
| EB | 11.2 | | 12.0 |
| m-xylene | 44.9 | | 47.9 |
| p-xylene | 19.0 | | 20.3 |
| o-xylene | 18.5 | | 19.8 |
| $C_9$ Aromatics | | 2.6 | |
| Wt. % Conversion to Non-Aromatics | | 0.1 | |
| Wt. % loss $C_8$ Aromatics | | 6.4 | |

I claim:

1. In a process for conversion of a mixture of aromatic compounds having eight carbon atoms, said mixture containing ethyl benzene and xylenes, to isomerize xylenes contained in said mixture and convert at least part of ethyl benzene so contained to xylene or to compounds readily separable by distillation from eight carbon atom aromatics; the improvement which comprises contacting such mixture of eight carbon atom aromatic compounds with a catalyst which comprises acid zeolite of the ZSM-5 type, acid zeolite ZSM-12 [or acid zeolite ZSM-21], *acid zeolite ZSM-35 or acid zeolite ZSM-38* in vapor phase and in the absence of added hydrogen at a temperature of about 500° F. to about 1,000° F.

*2. The process of claim 1 wherein said contacting is effected at a pressure in the range of 0 to about 1000 psig.*

*3. The process of claim 1 wherein said contacting is effected at atmospheric pressure.*

*4. The process of claim 1 wherein said contacting is effected at 150 psig.*

*5. The process of claim 1 wherein said contacting is effected at 200 psig.*

* * * * *